United States Patent
Luksch et al.

(10) Patent No.: US 8,784,021 B2
(45) Date of Patent: Jul. 22, 2014

(54) JIG DEVICE AND APPARATUS AND METHOD OF MAKING A DENTAL PROSTHESIS OR PATTERN THEREFOR

(75) Inventors: Derrick Luksch, South Beach, OR (US); Christophorus Luksch, Corvallis, OR (US)

(73) Assignee: O'Brien Dental Lab, Inc., Corvalis, OR (US)

( * ) Notice: Subject to any disclaimer, the term of this patent is extended or adjusted under 35 U.S.C. 154(b) by 1294 days.

(21) Appl. No.: 12/612,872

(22) Filed: Nov. 5, 2009

(65) Prior Publication Data

US 2011/0104642 A1    May 5, 2011

(51) Int. Cl.
*A61C 5/10* (2006.01)
*B23C 3/00* (2006.01)

(52) U.S. Cl.
USPC ........... 409/132; 409/164; 409/174; 409/198; 409/221; 433/51; 433/223; 269/7

(58) Field of Classification Search
USPC ................. 409/131–132, 164–165, 174, 189, 409/197–198, 219, 221; 433/51, 223; 269/7
IPC .......................................................... A61C 5/10
See application file for complete search history.

(56) References Cited

U.S. PATENT DOCUMENTS

| | | | | |
|---|---|---|---|---|
| 2,633,776 A | * | 4/1953 | Schenk | 409/132 |
| 2,676,499 A | * | 4/1954 | Walther | 408/1 R |
| 4,730,382 A | * | 3/1988 | Parsons | 29/563 |
| 4,904,348 A | * | 2/1990 | Domes et al. | 205/67 |
| 5,079,821 A | * | 1/1992 | Parsons | 29/424 |
| 5,116,174 A | * | 5/1992 | Fried et al. | 409/79 |
| 5,634,250 A | * | 6/1997 | Mihailovic | 29/26 A |
| 5,836,729 A | * | 11/1998 | Fink | 409/132 |
| 6,019,554 A | * | 2/2000 | Hong | 409/132 |
| 6,082,938 A | * | 7/2000 | Fink | 409/132 |
| 6,739,959 B2 | * | 5/2004 | Bodenmiller et al. | 451/364 |
| 6,915,178 B2 | | 7/2005 | O'Brien et al. | |
| 7,094,012 B1 | * | 8/2006 | Bang et al. | 409/221 |
| 7,234,938 B2 | * | 6/2007 | Bodenmiller | 433/51 |
| 7,252,466 B1 | * | 8/2007 | Roch | 409/187 |

FOREIGN PATENT DOCUMENTS

SU    1227373 A  *  4/1986

* cited by examiner

*Primary Examiner* — Daniel Howell
(74) *Attorney, Agent, or Firm* — John J. Connors; Connors & Assoc. PC

(57) ABSTRACT

A jig device holding a work piece is used with a milling machine that cuts from the work piece a prosthesis having a surface essentially free of defects. The jig device is inserted repeatedly into the machine in the same predetermined location, even upon inverting the jig device. This maintains the spatial relationship between the jig device and milling so, at start up, they are always in the same exact spatial relationship. The milling machine partially cuts through a first side of the work piece to form in the work piece a cavity having a surface part corresponding to at least a portion of the prosthesis being made. The jig device is then removed from the machine, inverted and reinserted into the machine at the same predetermined location. A support material is placed in the cavity prior to reinserting the jig device. Upon reinserting the jig device, the machine precisely cuts through an opposed side of the work piece to form within the work piece a prosthesis having a surface essentially free of defects. The prosthesis is supported within the work piece by the support material. The prosthesis and support material are separated to complete our method.

10 Claims, 10 Drawing Sheets

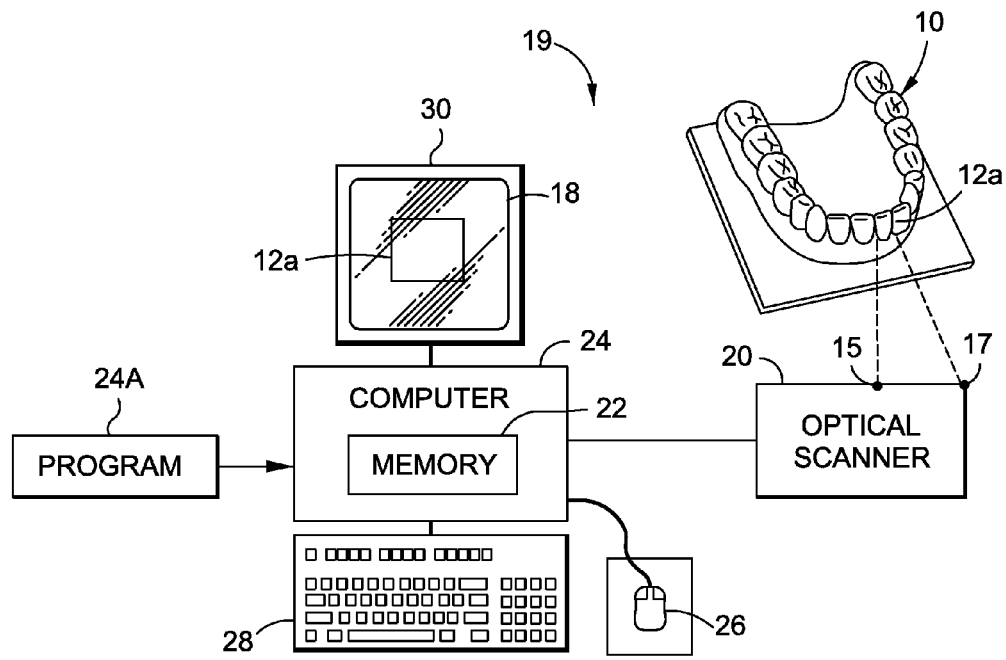
*Fig. 1B*
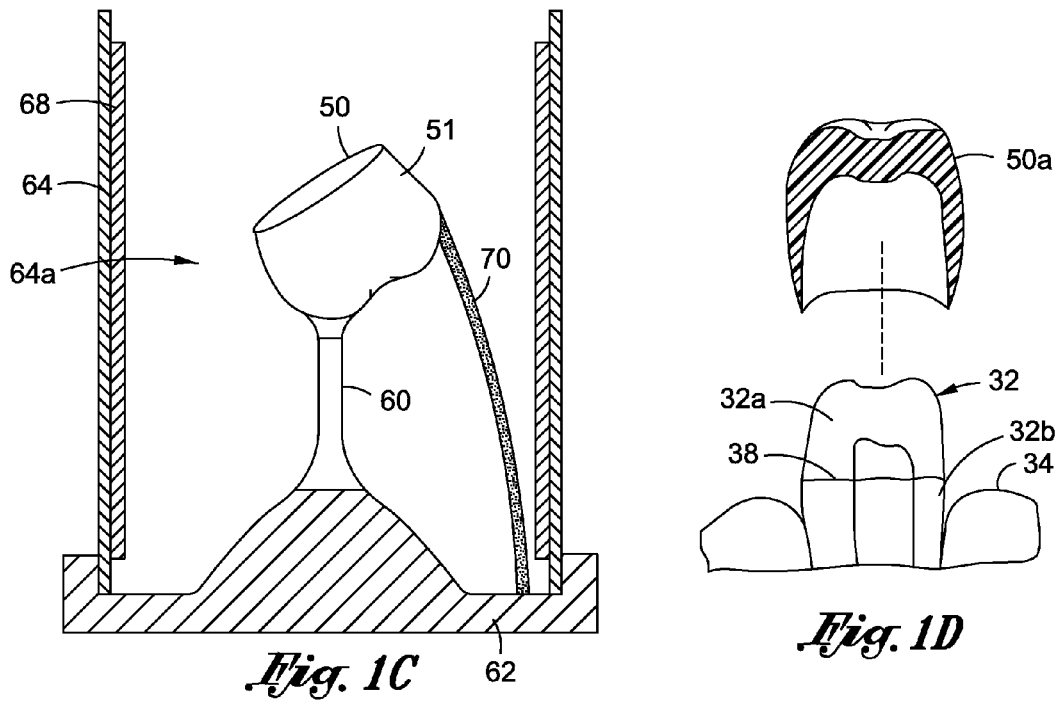
*Fig. 1C*
*Fig. 1D*

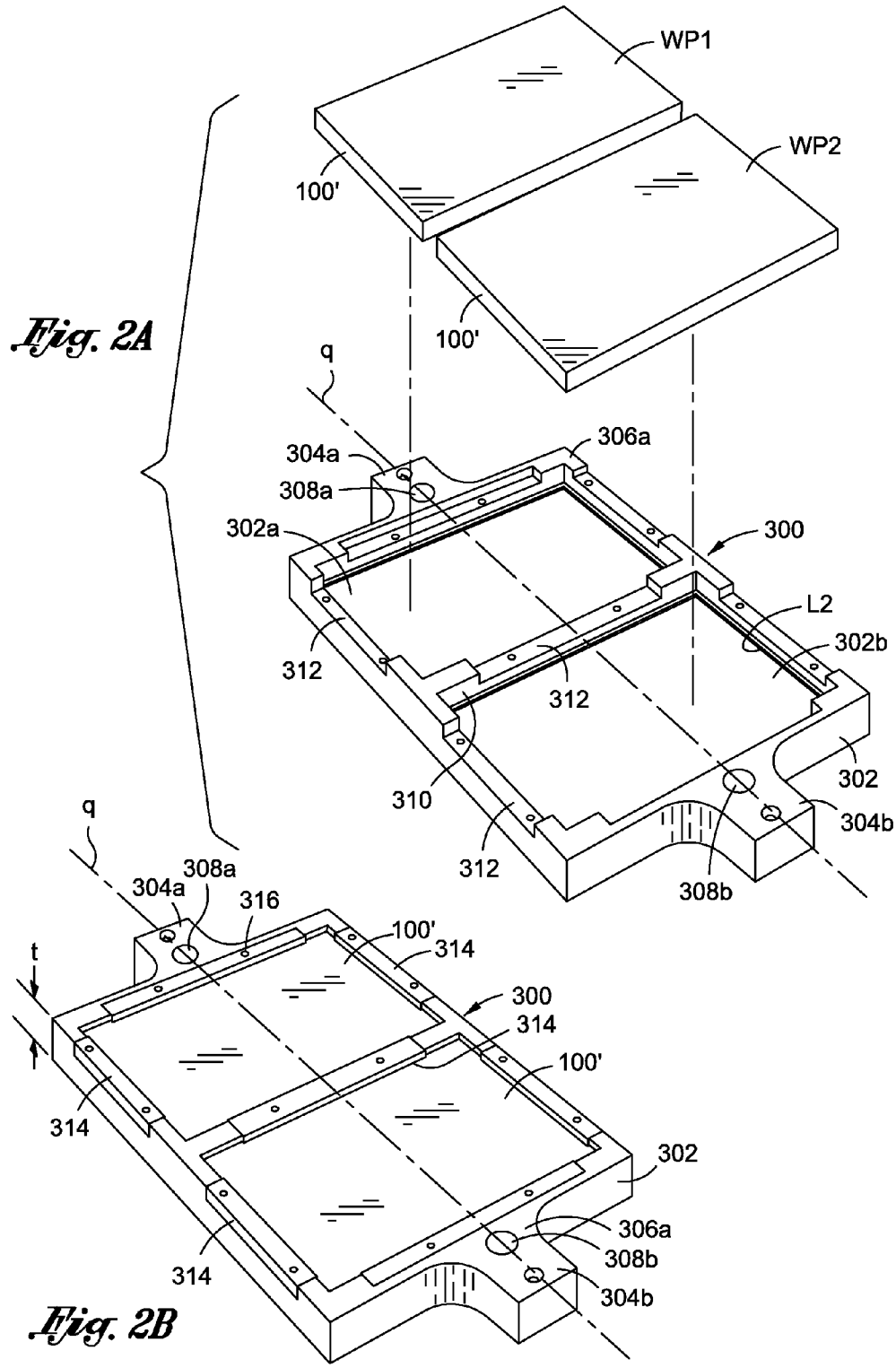

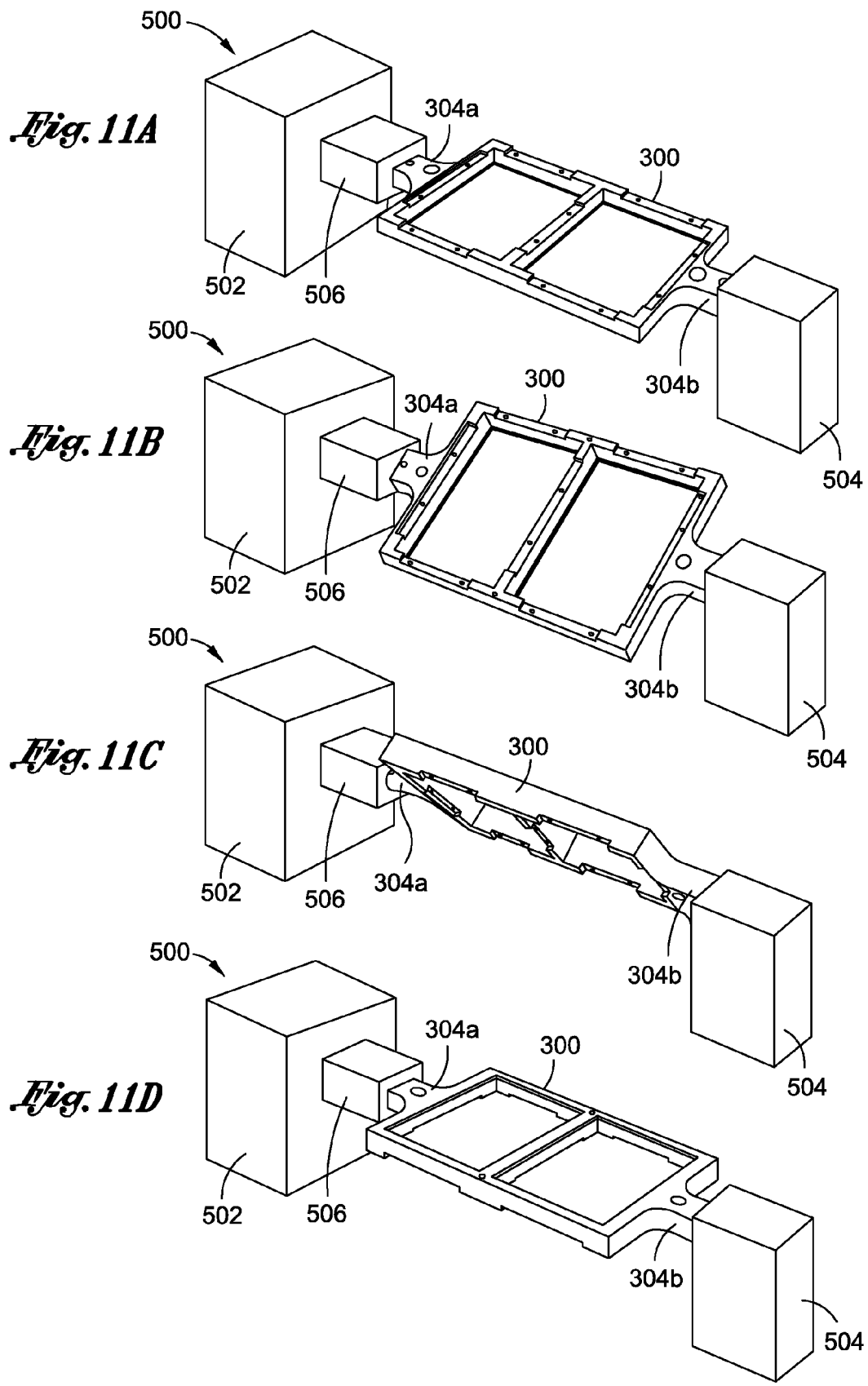

JIG DEVICE AND APPARATUS AND METHOD OF MAKING A DENTAL PROSTHESIS OR PATTERN THEREFOR

INCORPORATION BY REFERENCE

Any and all U.S. patents, U.S. patent applications, and other documents, hard copy or electronic, cited or referred to in this application are incorporated herein by reference and made a part of this application.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

In the claims, the words "prosthesis" or "prostheses" shall mean a dental prosthesis or a pattern for making a dental prosthesis.

The word "rectangular" includes square.

The words "substantially" and "essentially" have equivalent meanings.

BACKGROUND

Computer technology has advanced to the point where a dental prosthesis may be milled from a solid block of material based on three-dimensional digital data corresponding to a proposed shape of the dental prosthesis. All methods of production begin with a model of the patient's dentition. The dentist will first make an impression of a patient's existing dentition, including the teeth immediately above and to the side of the tooth structure to which the dental prosthesis is to be attached. After first cutting away any unwanted tooth structure, thereby preparing the tooth to which the prosthesis is to be attached, the dentist has the patient bite into an impression material forming a negative impression of the patient's dentition. The negative impression is then filled with dental die stone to make a model. This model should duplicate the occlusion surfaces between upper and lower aligned teeth and the configuration of the prepared tooth structure to which the dental prosthesis is to be attached. Currently there is a newer, less common method of creating a model of the patient's dentition utilizing a digital impression. With digital devices placed in the mouth and using cad/cam technology to produce the finished model, the need for a physical impression is no longer there. Two such systems currently in use in the United States would be the Itero System, manufactured by Cadent and the C.O.S. System from 3M Corporation.

The computer aided design equipment used to make a dental prosthesis has a scanner that is used to scan the surfaces of the model. Scanning may be accomplished either with optical techniques using laser or non-laser light or tactile techniques where a probe physically contacts the prosthesis's surface. The computer aided design equipment converts the model's surfaces into three-dimensional digital data corresponding to the physical shape of the model. This original data collected during scanning is then used to create an image of the proposed shape for the prosthesis on a screen of a computer monitor. The original image displayed on the monitor screen needs to be adjusted to modify the original image to correspond to the ultimate shape of the dental prosthesis. The computer aided design equipment is programmed to allow the technician, with the aid of a mouse and employing conventional point and click techniques, to change the shape of the image.

Because the data originally collected during scanning isn't precise enough to make the dental prosthesis directly based on this data, the technician can and does make adjustments to the data originally provided by the scanner so that the dental prosthesis, at least in theory, fits properly into the patient's mouth. After making such adjustments to the data collected by the scanner, the adjusted three-dimensional digital data is then forwarded to an automatic milling machine that then mills away the unwanted material from a work piece to form the dental prosthesis. Typically, the work piece is a block of material comprised of ceramic, titanium, or a composite plastic material. Conventional investment casting is also used to make a dental prosthesis and a wax pattern may be milled from a work piece of wax that is then used in the investment casting process.

SUMMARY

Our jig device and apparatus, and method of making a prosthesis, have one or more of the features depicted in the embodiments discussed in the section entitled "DETAILED DESCRIPTION OF SOME ILLUSTRATIVE EMBODIMENTS." The claims that follow define our jig device and apparatus and method of making a prosthesis, distinguishing them from the prior art; however, without limiting the scope of our jig device and apparatus and method of making a prosthesis as expressed by these claims, in general terms, some, but not necessarily all, of their features are:

One, in our method a milling machine mills from a two-sided work piece a dental prosthesis essentially free of defects. The milling machine has a cutting tool that terminates at a cutting tip that has, at a start position, an exact spatial relationship with respect to a working reference plane of the milling machine. A first side of the work piece is presented to the cutting tool, and starting from the start position, the cutting tool is operated to partially cut through the first side to form in the work piece a cavity having a surface part corresponding to at least a portion of the prosthesis being made. A floor of the cavity may include the surface part corresponding to at least a portion of the prosthesis being made. The work piece may be a substantially solid block having opposed, substantially parallel, planar sides, and it may be made of wax, metal, ceramic, or a plastic.

Two, the cavity is at least partially filled with a support material and the work piece is inverted to present to the cutting tool a second or opposite side of the work piece. The work piece is inverted in a manner so that the surface part corresponding to at least a portion of the prosthesis being made, namely, the cavity is in an exact predetermined position with respect to the working reference plane of the milling machine. Starting from the start position, the cutting tool is positioned to overlie the second side directly over and opposite an un-milled segment of the work piece that supports the surface part corresponding to the partially milled prosthesis being made. When so positioned, the cutting tool is now operated to completely cut through the second side of the work piece and form completely a prosthesis with a surface essentially free of defects. From each side of the work piece, the cutting tool may only cut into the work piece to a maximum depth corresponding substantially to an optimum point of dissection of the prosthesis being made and no further. This defect free prosthesis is supported within the work piece by the support material, and the prosthesis is separated from the work piece as the final step in our method.

Three, a jig device may be used to hold the work piece in the milling machine at a predetermined location so the jig device and milling machine are in an exact spatial relationship to enable the milling machine to precisely mill from the work. Our jig device is detachably mounted to a planar tabletop of the milling machine and can be detached, inverted, and re-inserted after milling the first side of the work piece into the machine at the same predetermined location. The jig device and milling machine may have interactive elements that enable the jig device to be repeatedly inserted, removed and inverted, and then reinserted into the milling machine at the same predetermined location with each insertion, or reinsertion after inverting. Thus, the jig device and milling machine are always in the same exact spatial relationship to enable the cutting tool to precisely cut from the work piece a prosthesis having a surface essentially free of defects. The jig device, when inserted or reinserted into the milling machine, may be in a first plane and the cutting tool may be at a right angle to this first plane. For example, our jig device when inserted or reinserted into the milling machine may be substantially oriented in a horizontal plane and the cutting tool may be substantially oriented in a vertical plane.

In one embodiment, our jig device is substantially symmetrical about a central longitudinal line and substantially symmetrical about a central latitudinal line. Our jig device may include a frame structure in which the work piece is seated, where the frame structure may have opposed planar parallel surfaces that are, for example, spaced apart a distance substantially from ½ to 2 inches. There may be clamping means along the frame that keep the work piece in a stationary position within a space in the frame structure and an alignment arrangement along the frame member that provides locating structure to enable the jig device to engage locating structure on the tabletop. The alignment arrangement may comprise aligned openings positioned to intersect and engage a pair of aligned vertical post elements projecting outward from the tabletop directly or indirectly by way of a platform fixedly attached to the tabletop. Each post element slides into an individual opening upon mounting the jig device to the tabletop. The clamping means may include a plurality of detachable members that upon being fastened to the frame hold the work piece in the stationary position.

Four, our apparatus makes a prosthesis from a two-sided work piece, and it includes a milling machine and a holder for the work piece that enables the work piece to be inverted. Our jig device and milling machine have interactive elements that enable the jig device to be repeatedly inserted, removed and inverted, and then reinserted into the milling machine at the same predetermined location with each insertion, or reinsertion after inverting. Consequently, our milling machine may be programmed to operate so the cutting tool precisely cuts from the work piece a prosthesis having a surface essentially free of defects. The work piece is moved from a first position, presenting to the milling machine's cutting tool a first side of the work piece, to a second position presenting to the cutting tool a second side of the work piece. A drive mechanism for the milling machine is initially operated when the work piece is in the first position so the cutting tool partially cuts through the first side of the work piece, to drill away a substantial portion of material from the work piece, while avoiding penetrating through the work piece with the tip of the cutting tool. This forms in one side of the work piece a cavity having a surface part corresponding to at least a portion of the prosthesis being made. The drive mechanism may move the tabletop from the start position laterally along the working reference plane in one or the other of orthogonal directions and rotates and moves the cutting tool from the start position towards and away from the tabletop along a straight line following the tool's longitudinal centerline. The drive mechanism returns the cutting tool and the tabletop to their respective start positions after partially cutting through the one side of the work piece to enable filling the cavity at least partially with the support material. The drive mechanism is operated to completely cut through the opposite side of the work piece after filling the cavity with support material to finish making a prosthesis having a surface essentially free of defects.

In one embodiment of our apparatus, the milling machine's planar tabletop may be mounted to move laterally in a straight line along the working reference plane in one or the other of orthogonal directions. The cutting tool may be mounted to rotate and to move towards and away from the tabletop along a straight line. The cutting tool's longitudinal centerline may be normal to the working reference plane and intersects a reference point on the working reference plane when the tabletop and cutting tool are in the start positions. A locating structure for positioning the jig device in a predetermined location is on the tabletop. The locating structure enables an operator to manually insert the jig device into the milling machine at a predetermined location so the jig device and milling machine are in an exact spatial relationship allowing the cutting tool to precisely cut from the work piece the prosthesis being made. This locating structure may comprise a detachable platform including a pair of aligned vertical post elements projecting outward from the tabletop. It may be designed to position the jig device with a surface of the jig device adjacent, and substantially parallel to, the planar tabletop.

These features are not listed in any rank or order nor is this list intended to be exhaustive.

DESCRIPTION OF THE DRAWING

Some embodiments of our jig device and apparatus, and method of making a prosthesis, are discussed in detail in connection with the accompanying drawing, which is for illustrative purposes only. This drawing includes the following figures (Figs.), with like numerals indicating like parts:

FIG. 1B is a schematic diagram of computer aided design equipment used in the making of a digitized image of a prosthesis.

FIG. 1C is a schematic cross-sectional view showing a wax pattern of a crown type dental prosthesis positioned in a casting ring used in investment casting.

FIG. 1D is a side elevational view of a patient's prepared tooth structure to which a crown type dental prosthesis made by our method is being attached.

FIG. 2A is an exploded perspective view of one embodiment of our jig device.

FIG. 2B is a perspective view of our jig device shown in FIG. 2A and assembled to hold a pair of wax work pieces.

FIGS. 11A through 11D are perspective views of another embodiment of our apparatus where our jig device is mounted to be automatically rotated to invert our jig rather than removed from our apparatus and manually inverted.

DETAILED DESCRIPTION OF SOME ILLUSTRATIVE EMBODIMENTS

FIG. 1 Prior Art

Figure 1:
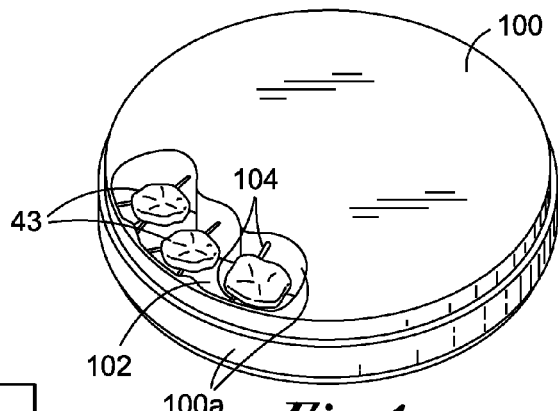
FIG. 1 is a perspective view of partially formed prostheses milled from a work piece according to conventional milling processes.

The problem with conventional milling machines and methods for making a dental prosthesis is the time consuming manual hand work required, after completion of the milling process, to eliminate surface defects. In order to mill from a work piece 100 (FIG. 1) an object with an entirely complete organic shape (indefinable by a mathematical model) requires the milled object being manufactured to be physically suspended while avoiding all contact with source material (wax, plastic, metal, etc.) from the work piece. Traditionally, milling any dental prosthesis from any material requires support such as pins or positioning runners to hold the partially formed prosthesis in place while the prosthesis is being milled out of the work piece 100. Illustrated in FIG. 1 is a milled work piece 100 showing a number of dental prostheses 43 made in the conventional manner and suspended within an opening 102 formed in the body of the work piece. Arms 104 formed during milling extend across the space of the opening 102 between each individual prosthesis 43 and the body 100a of the work piece 100 to keep the prostheses suspended in position until a technician breaks the arms to detach each individual prosthesis from the body of the work piece. This leaves on each individual prosthesis residual surface defects that must be hand polished to eliminate. In such prior art manufacturing methods the work piece is held immobile in the same stationary position throughout the entire milling process.

General

Our method avoids the formation of any residual surface defects on the prosthesis, thereby eliminating any hand working after milling a work piece. In our method the prosthesis is manufactured in a completed three-dimensional organic shape without using positioning pins or any point of attachment between the finished prosthesis and the body of the work piece. We are able to mill a completed three-dimensional organic shaped prosthesis by splitting in half a CAD/CAM milling pattern corresponding to the external and internal surfaces of the prosthesis being made. FIGS. 4D through 4F illustrate an exemplary milling pattern MP in phantom lines representing a three-dimensional digital data image stored in the memory a computer of a crown prosthesis 50a.

Instead of keeping the work piece immobile through the entire milling process in our method about half of the milling pattern is milled in one side of the work piece and the other half in the other side, each as independent and separate operations. In other words, the prosthesis is formed in approximately half sections in two steps. To do this a work piece is first milled from one side, and then the work piece is inverted to present for further milling from the opposite side of the work piece. We first establish and define the optimum point of dissection OPD (FIG. 4D) of the milling pattern MP. The optimum point of dissection OPD is the horizontal apex (determined by the milling instruction provided by a microprocessor of a milling machine for any individual prosthesis being made) of any shape, and the maximum vertical limit of contact that can be reached between source material provided by the work piece and the cutting tool of the milling machine. The optimum point of dissection OPD can be compared to, and is similar to, the earth's equator. It is an imaginary plane IP (FIG. 4D) that follows the outermost points along the circumference of the prosthesis being made, essentially splitting the milling pattern MP into approximately half sections that are distorted hemispheres H1 and H2, each having a reference milling plane, namely, the reference milling plane RMP 1 for the hemisphere H1 (FIG. 4E) and the reference milling plane RMP 2 for the hemisphere H2 (FIG. 4F). The optimum point of dissection OPD is mutually exclusive and unique to the individual shape of the prosthesis being made, and therefore cannot be predetermined or established until the milling pattern MP is complete as discussed subsequently in connection with FIG. 1B.

To mill a complete three-dimensional object such as a dental prosthesis without positioning pins or the like, starting at one of the reference milling planes RMP1 or RMP2, we first cut into one side of the work piece down to the optimum point of dissection OPD forming a cavity that includes a portion of the prosthesis being made. Once the optimum point of dissection OPD has been reached, which corresponds to forming about half the milling pattern MP, for example the hemisphere H2, the cavity is at least partially filled with the support material SM. This support material SM is a substitute for the milled away work piece material. In our method, the support material SM filling the cavity acts like a stationary sabot to hold the prosthesis being made immobile within the work piece, maintaining the prosthesis' exact position within the work piece. The work piece may be held within a holding device that may be repositioned, exposing the opposite side of the work piece to the cutting tool.

Milling is continued with respect to the second reference milling plane RMP 2 by cutting into the opposite side of the work piece to form an object corresponding to the other approximately half of the milling pattern MP, in this example the hemisphere H2. Milling from the reference milling plane RMP2 down to the optimum point of dissection OPD physically separates the now completed milled prosthesis from the source material provided by the body of the work piece. The physical object corresponding to the milling pattern MP is now only held in place by the lateral pressure provided by the support material SM. With milling over, the completely milled prosthesis is separated from the support material SM, free of any linear planes, positioning pin artifacts or molding flash commonly found when using conventional methods. Using the support material SM as a "dental sabot" allows for full contour and complete milling of a finished prosthesis without hand finishing or removal of positioning pins and/or runners.

For example, our method and apparatus may be used to make a wax pattern for use in the lost wax process of making a dental prosthesis such as the crown 50a corresponding to the wax pattern 50. An example of a suitable work piece for use in the lost wax process is illustrated in FIGS. 4A and 4B and designated by the numeral 100'. This work piece 100' is a substantially solid block of wax having a planar side A (FIG. 4A) and opposed planar side B (FIG. 4B), which are substantially parallel. The work piece 100' may have different shapes such as, for example, circular, rectangular, hexagonal, etc.

Lost Wax Process

As shown in FIG. 1B, a digital file of a three-dimensional image of the dental prosthesis is first made in accordance with conventional techniques from a model of a patient's dentition. A model 10 of a patient's lower jaw dentition is shown in FIG. 1B. A patient's upper jaw dentition model may also used to collect prosthesis surface data, but is not shown. For purposes of illustration as shown in FIG. 1D a prepared stump 32 to which a crown type 50a dental prosthesis is to be attached includes a drilled away portion 32a. The model 10 includes a replicate 32a of the stump 32 to which the crown type dental prosthesis 50a is to be attached.

As shown in FIG. 1B, computer aided design equipment 19 creates an image of a dental prosthesis based on data collected from the model 10. The equipment 19 includes an optical scanner 20 that scans the surfaces of the model of a patient's dentition by directing a beam of light from a source 17 at the model's surfaces, for example, at prosthesis surfaces of the model stump 32a. The reflected light represents information corresponding to the contours of these surfaces. This information is collected by a sensor 15 and then stored in the memory 22 of a computer 24 as three-dimensional digital data. Various images of a dental prosthesis are displayed on the screen 18 of a monitor 30 connected to an output 32 of the computer 24 based on the data originally collected by the scanner 20. These images, and the corresponding data creating these images, are modified by the technician using conventional input devices such as a mouse 26 and keyboard 28 to interact with, and modify, the originally collected three dimensional digital data.

The numeral 12a is an image displayed on the screen 18 corresponding to the actual prosthesis structure that is to be attached to the stump 32 (FIG. 1D) prepared by a dentist for a dental prosthesis. The image 12a is created by optically scanning the surface of the replicate 32a of the stump 32 and manipulating the collected information of the surface contours, creating the image 12a in accordance with a program 24a that controls processing of the data by the computer 24. As depicted in FIG. 1B, an image 12a of the crown 50a to be attached to the stump 32 is displayed on the monitor's screen 18. Through the use of the mouse 26 and keyboard 28 the technician can change parameters such as die spacer, minimum thickness of the prosthesis, contact points, grooves, cusp overlays and marginal ridges.

Using our apparatus as discussed subsequently, a wax pattern 50 (FIGS. 1C and 8) of the prosthesis being made is first milled from a work piece 100' (FIGS. 4A and 4B) made of wax. This wax pattern 50 is based on the data collected during optical scanning and is used in the conventional investment casting process to make, for example, a crown type dental prosthesis 50a as illustrated in FIG. 1D. As shown in FIG. 1C, the wax pattern 50 is attached to a sprue 60 made of wax material. This sprue 60 is mounted to a raised conical portion of a rubber base 62 and a metal ring 64 lined with a sheet 68 of ceramic fiber paper that is seated on the base. Preferably, a wax rod 70 extends from a side portion of the wax pattern 50 to the base 62. The hollow interior 64a of the ring 64 and base 62 is then filled with the investment material, for example, a plaster, that is allowed to dry. After drying the assembly of the base 62, ring 64 and mounted wax pattern 50 is inverted and the base removed. The sprue 60 and wax pattern 50 are next removed by burning them away so that the casting is formed with a hollow cavity (not shown) into which a molten metal or ceramic material is forced to form the crown 50a.

FIGS. 1A Through 10

In our method a conventional milling machine 200 (FIG. 10) cuts from the two-sided work piece 100' a prosthesis essentially free of surface defects. Model OM2 sold by Haas is an example of a three-axis machine that may be used, however, up to six-axis machines may be used to practice our method. This machine 200 has a planar, horizontal tabletop 202 and a vertically oriented cutting tool 204 above the tabletop. The cutting tool 204 may be a drill including a drill bit 206 terminating at a cutting tip 206a and detachably connected to a spindle 208. A drive mechanism 210 for the milling machine 200 rotates the spindle 208 and bit 206 (FIGS. 4 and 7) as a unit, moves the spindle towards and away from the tabletop 202 along a straight line following the drill bit's longitudinal centerline z, and concurrently moves the tabletop laterally in a straight line along a working reference plane WRP (FIGS. 4A and 4B) in one or the other of the orthogonal directions x and y. In this example, the working reference plane WRP is coextensive with the tabletop 202. Both the cutting tool 204 and tabletop 202 have a start position where the tip 206a of the cutting tool has an exact spatial relationship with respect to the working reference plane WRP of the milling machine 200. In the start positions for both the cutting tool 204 and tabletop 202, the cutting tool's longitudinal centerline z is normal to the working reference plane WRP and intersects a reference point a on the working reference plane. In making dental prostheses tolerances are typically controlled to within 0.001 inch.

Figure 4:
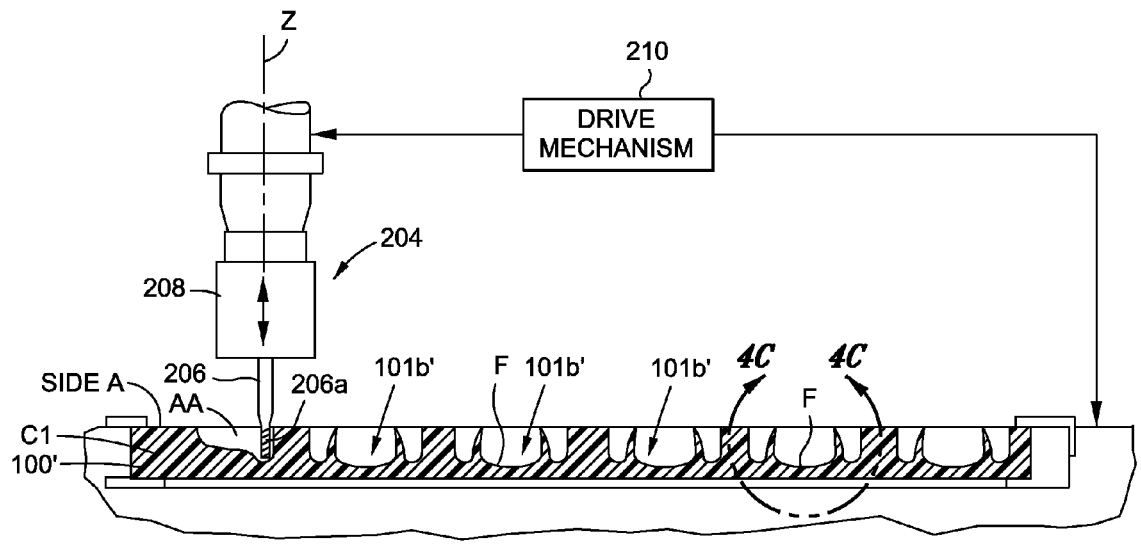
FIG. 4 is a cross-sectional view of portions of our apparatus showing a cutting tool of our apparatus partially cutting into one side of a work piece held by our jig device that is attached to the tabletop of the apparatus.
Figure 4C:
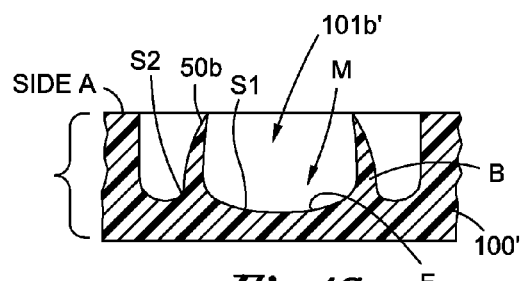
FIG. 4C is an enlarged fragmentary cross-section view taken along line 4A of FIG. 4.
Figures 4D, 4E, 4F:
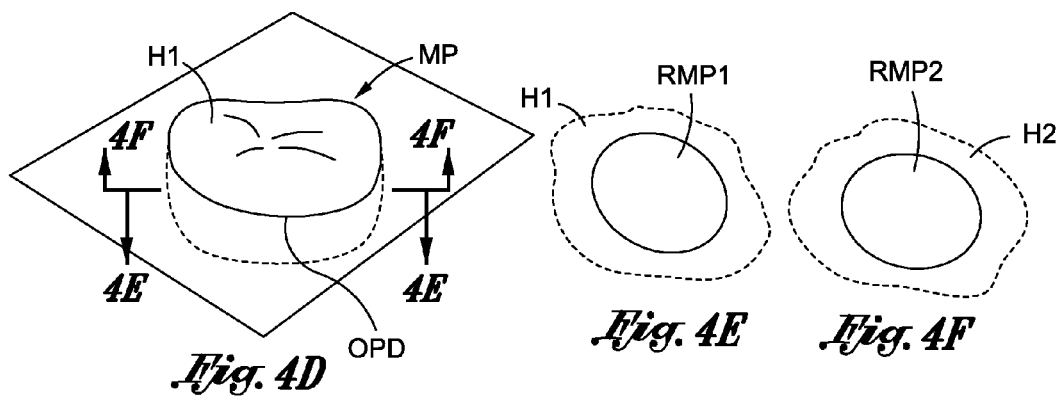
FIG. 4D is a perspective view in phantom lines depicting a three-dimensional digital data image of a dental prosthesis stored in the memory a computer.
FIG. 4E is a cross-sectional view taken along line 4E-4E of FIG. 4D.
FIG. 4F is a cross-sectional view taken along line 4F-4F of FIG. 4D.
Figure 4A:
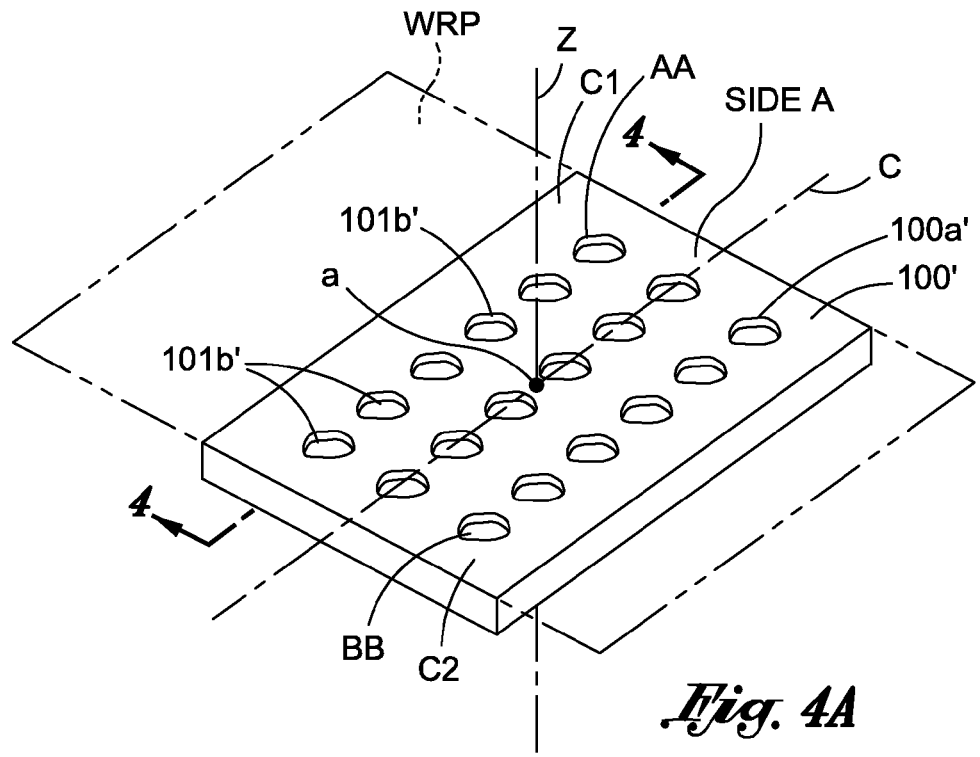
FIG. 4A is a perspective view of a rectangular work piece held by our jig device shown in FIGS. 2A and 2B, showing side A of the work piece.
Figure 4B:
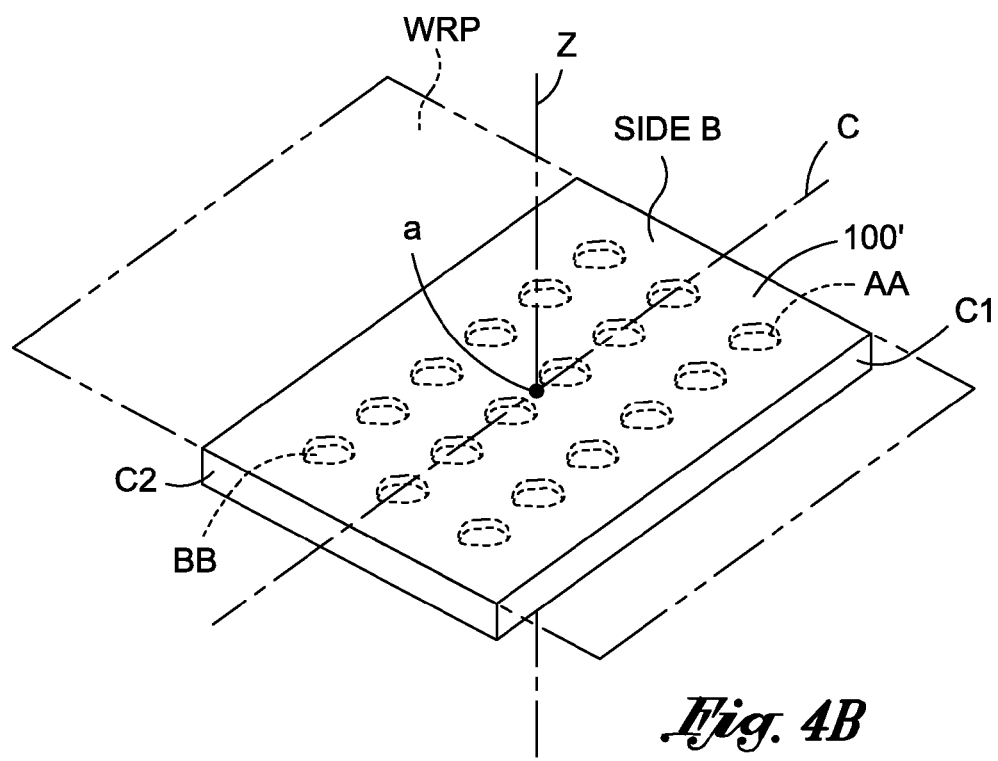
FIG. 4B is a perspective view of the rectangular work piece depicted in FIG. 4A inverted to show its side B.

As depicted in FIG. 4, side A of the work piece 100' is initially presented to the cutting tool 204 and, starting from the start position, the cutting tool partially cuts through the side A to form in the work piece one or more cavities 101b' having a surface part corresponding to at least a portion of the prosthesis being made. For example, in FIGS. 4 through 9, crowns are being manufactured where each individual crown 50a is custom made to fit snugly on an individually prepared tooth stump (FIG. 1D). In the embodiments disclosed herein, and as best depicted in FIGS. 4 and 4C, a floor F of an individual cavity AA is a surface part corresponding to at least a portion of the prosthesis being made. Referring to FIG. 4A, the milled side A has a plurality of cavities 101b' formed therein with, for example, a cavity AA in the corner C1 and a cavity BB in the corner C2. In the first stage of our method as depicted in this example, the entire interior surface S1 (FIG. 4C) of the crown 50a and part of the exterior surface S2 of the crown are milled into the side A of the work piece 100'. Also formed during this first stage is a lower edge 50b (FIG. 4C) of the crown 50a, that is, the perimeter or margin defining an open mouth M of the base B of the crown. In one embodiment of our method and apparatus, the milling machine 200 is programmed to cut into side A of the work piece 100' to a maximum depth corresponding to substantially the greatest diameter (optimum point of dissection) of the prosthesis being made and no further. The cutting tool 204 and tabletop 202 are returned to their start positions after partially forming the prosthesis.

Figure 5:
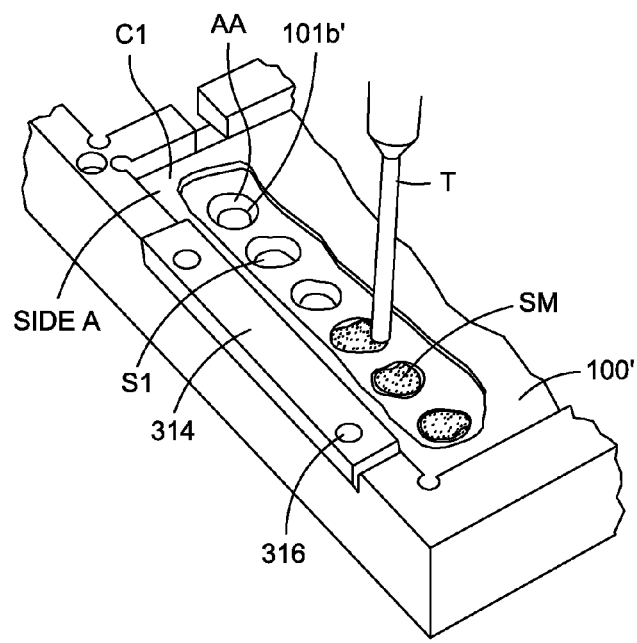
FIG. 5 is a perspective view showing the one side A of the work piece illustrated in FIG. 4A after being partially drilled to form a plurality of cavities, each having a surface part corresponding to at least a portion of the prosthesis being made.
Figure 6:
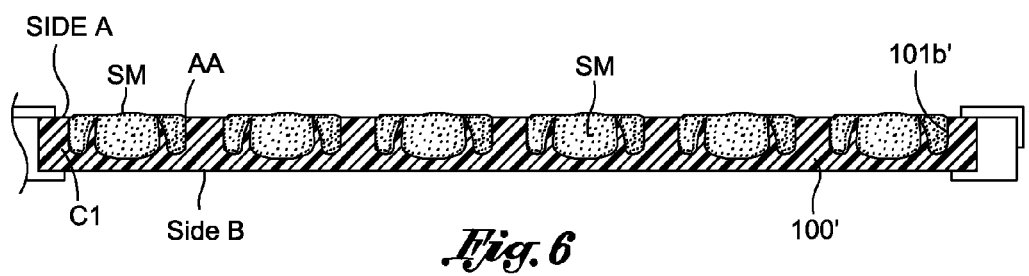
FIG. 6 is a cross-sectional view of the drilled work piece of FIG. 5 filled with a support material.

As depicted in FIGS. 5 and 6, the cavities 101b' formed in the one side A of the work piece 100' are at least partially filled with a support material SM. As best shown in FIG. 6, the support material SM fills the interior of the partially formed prosthesis and covers the open mouth M, typically filling the entire cavity up to about the surface of side A. The support material SM may be contained within a tube T and may be dispensed manually or automatically. This support material SM may be a gel that hardens shortly after being deposited in the cavity, but is not an adhesive that binds to surfaces of the partially milled work piece 100'. Consequently, the support material SM may be easily separated from the finished prosthesis, which will be free of surface defects. A suitable support material SM is, for example, Elite HD sold by Zhermack.

Figure 7:
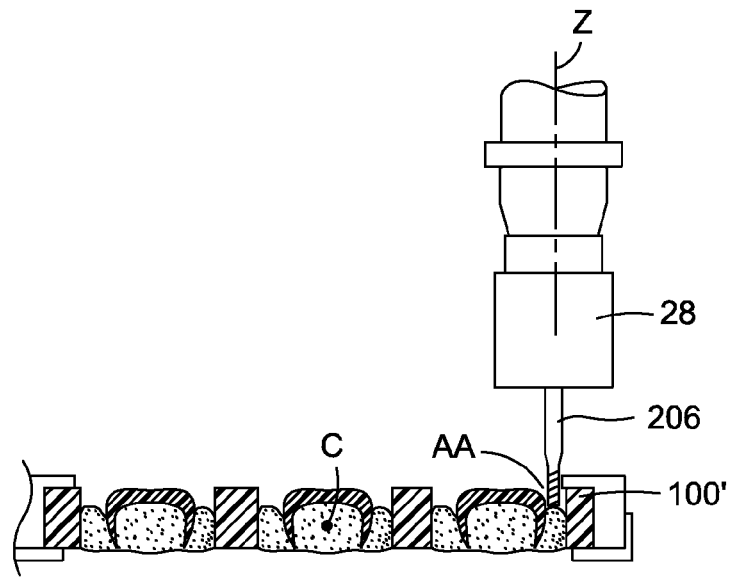
FIG. 7 is a cross-sectional view similar to FIG. 4 with our jig device holding the drilled work piece filled with a support material, inverted and attached in the same location as depicted in FIGS. 3A, 3B, and 4, showing the cutting tool of our apparatus cutting into side B of the work piece to make a prosthesis having a surface essentially free of defects.
Figure 8:
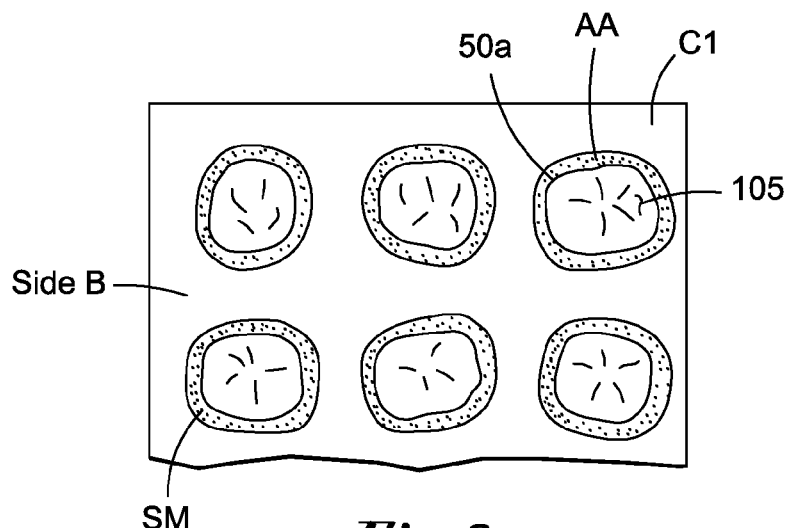
FIG. 8 is a top plan view of the work piece held by the jig device in the inverted position illustrating the support material filling the cavities to support the completely milled prostheses that are suspended within individual cavities.
Figure 9:
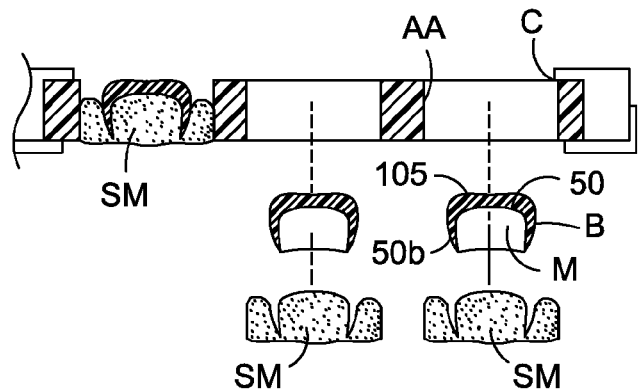
FIG. 9 is a cross-sectional view illustrating separating the prostheses made by our method from the work piece.

As depicted in FIGS. 4B and 7, in the next stage of our method, the work piece 100' is inverted to present to the cutting tool 204 the second side B of the work piece 100'. The work piece 100' is inverted in a manner so that the surface part corresponding to at least a portion of the prosthesis being made is in an exact predetermined position with respect to the working reference plane WRP. Referring to FIG. 4A, in the start position the side A lies in the working reference plane WRP with the centerline z of the bit intersecting point a, which corresponds to the center of the work piece. Upon inverting, the work piece 100' is rotated 180° about its centerline C. This repositions side B so it now lies in the working reference plane WRP with its center remaining in the same relative position with respect to the cutting tool 204 in the start position so the centerline z of the bit 206 intersects the work piece's center at point a. In this inverted position as depicted in FIG. 4B, the cavity AA shown in dotted lines now faces downward with its mouth M adjacent the table top 202 and side A substantially parallel to the surface 202a of the table top 202. The corners C1 and C2 and cavities AA and BB therein are now repositioned but in precise predetermined locations with respect to the start positions of the cutting tool 204 and tabletop 202. Consequently, the cutting tool 204 is moved from its starting position into an overlying orientation with respect to a repositioned cavity, for example, cavity AA. When the work piece 100' is thus inverted, repositioning occurs so that the cutting tool 204 upon moving from the start position is positioned to overlie the second side B and aligned opposite a segment 103 integral with the body 100a' and having an internal surface contoured as an individual surface part corresponding to at least a portion of the prosthesis being made portion, for example, the floor F of the cavity AA. The drill bit 206 is advanced by the drive mechanism 210 so the tip 206a cuts into side B and mills away the segment 103 to form the top surface of the prosthesis being made, for example, the surface 105 of the crown 50a. The cutting tool 204 now completely cuts through the second side B of the work piece 100' so the prosthesis formed is suspended by the support material SM and its surface is essentially free of defects. At this stage of our method as depicted in FIGS. 7 and 8, this prosthesis free of surface defects is supported within the work piece by the support material SM. The prosthesis free of surface defects is finally separated from the work piece 100' and support material as depicted in FIG. 9. This may be done manually or automatically.

Milling Machine and Jig Device Combination

Figure 1A:
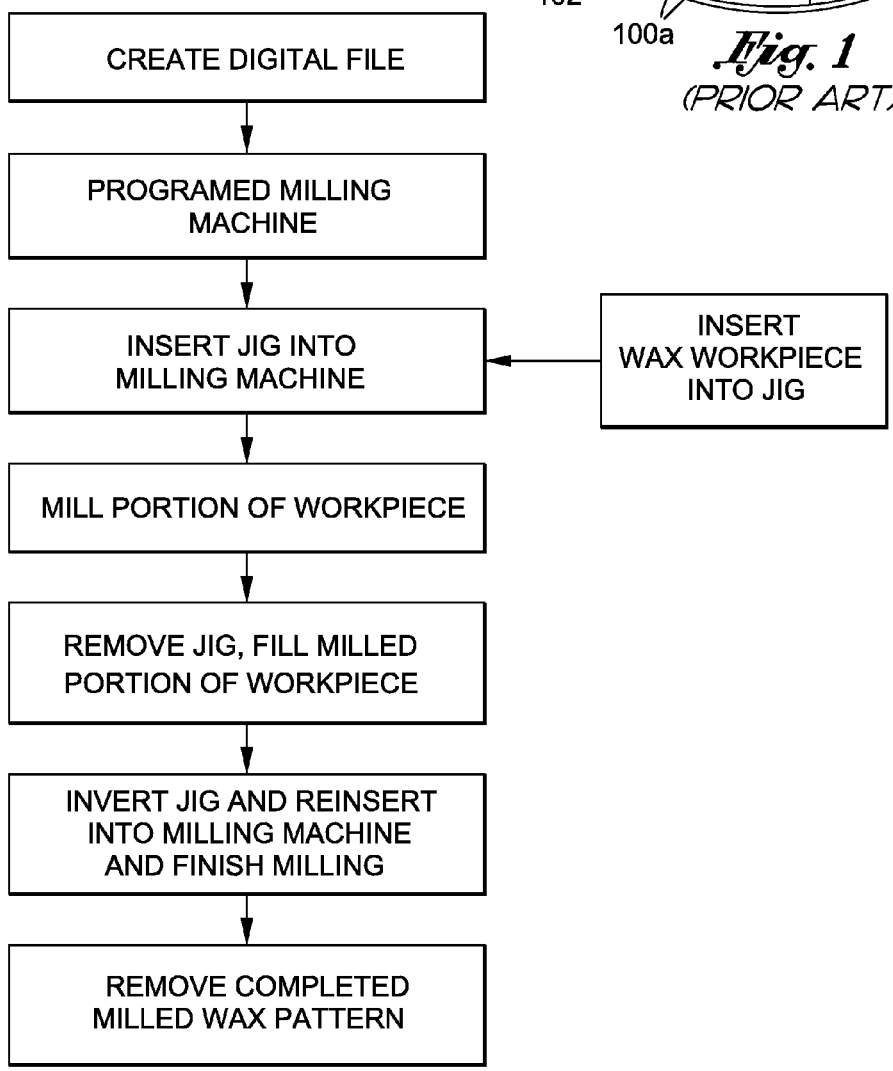
FIG. 1A is a schematic flow diagram illustrating one embodiment of our method of making a prosthesis.

As schematically illustrated in FIG. 1A, in one embodiment of our apparatus designated by the numeral 400 (FIG. 10) a jig device is used to hold a work piece. In one embodiment of our jig device designated by the numeral 300 and shown in FIGS. 2A through 3B, a pair of two-sided rectangular work pieces WP1 and WP2 is held in our jig device 300. The jig device 300 and milling machine 200, each time at start up, are in the exact same predetermined spatial relationship when cutting from either side of the work pieces WP1 and WP2. To achieve this the jig device 300 is fastened in the same predetermined location to the tabletop 202 each time a work piece is cut, regardless of the side of the work piece being milled. In accordance with our method, the cutting tool 204 partially cuts through the one side of the work pieces WP1 and WP2 to form in the work pieces individual cavities, each cavity having a surface including only a portion of the prosthesis being manufactured. What fraction of or portions is determined on a case-by-case basis depending on the specific configuration of the prosthesis being made.

The jig device 300 is detachably mounted on a platform 402 fixed to the surface 202a of the tabletop 202. After partially cutting through one side of each work piece WP1 and WP2, our jig device 300 is removed from our apparatus 400. The cavities formed in the work pieces WP1 and WP2 may be filled with the support material SM prior to removing the jig device 300 from the milling machine or after removing the jig device 300 from our apparatus 400. Support material SM is allowed to cure, if necessary, so it adheres with sufficient strength to the bodies of the pieces WP1 and WP2 to support the prostheses upon completion of the milling process. After the cavities formed in the work pieces WP1 and WP2 are filled with the support material SM, the jig device 300 is then inverted and reinserted into our apparatus 400. The cutting tool 204 is manipulated by the drive mechanism 210 to complete cutting away material from the two opposite sides of the work pieces WP1 and WP2, forming a series of prostheses, each with a surface essentially free of defects as discussed above. The support material SM is manually removed to separate the prostheses from the body of the work pieces WP1 and WP2.

Jig Device

As shown in FIGS. 2A and 2B, the jig device 300 includes a frame member 302 that provides a pair of adjacent rectangular spaces 302a and 302b into which the two-sided work pieces WP1 and WP2 are individually inserted and fit snugly therein. In the embodiment illustrated, the frame member 302 is substantially rectangular with a pair of opposed ears 304a and 304b along a longitudinal centerline q of the jig device 300 and a pair of opposed planar parallel surfaces 306a and 306b spaced apart a distance substantially from 1 to 2 inches. An alignment arrangement along the frame member 302 comprising aligned holes 308a and 308b along the centerline q of our jig device 300, one hole in each ear 304a and 304b. A central partition member 310 divides the frame 302 into two rectangular spaces 302a and 302b substantially of the same dimensions. For example, each spaces 302a and 302b defines an open area substantially from 4.5 to 5.5 square inches. These spaces 302a and 302b each have a rectangular ledge L1 and L2, respectively, which is adjacent and substantially flush or level with the one surface 306b of the frame member 302. The other surface 306a of the frame member 302 has a number of recesses 312 in which clamps 314 are fastened by screws 316. Initially the clamps 314 are removed and the rectangular work pieces WP1 and WP2, each one having about the same dimensions as an individual open space, are individually inserted into the spaces 302a and 302b. The ledges L1 and L2 support the inserted work pieces WP1 and WP2 and the clamps 314 are reattached to the frame member 302 by the screws 316 to keep the work pieces in place throughout the milling process.

Apparatus

Figure 10:
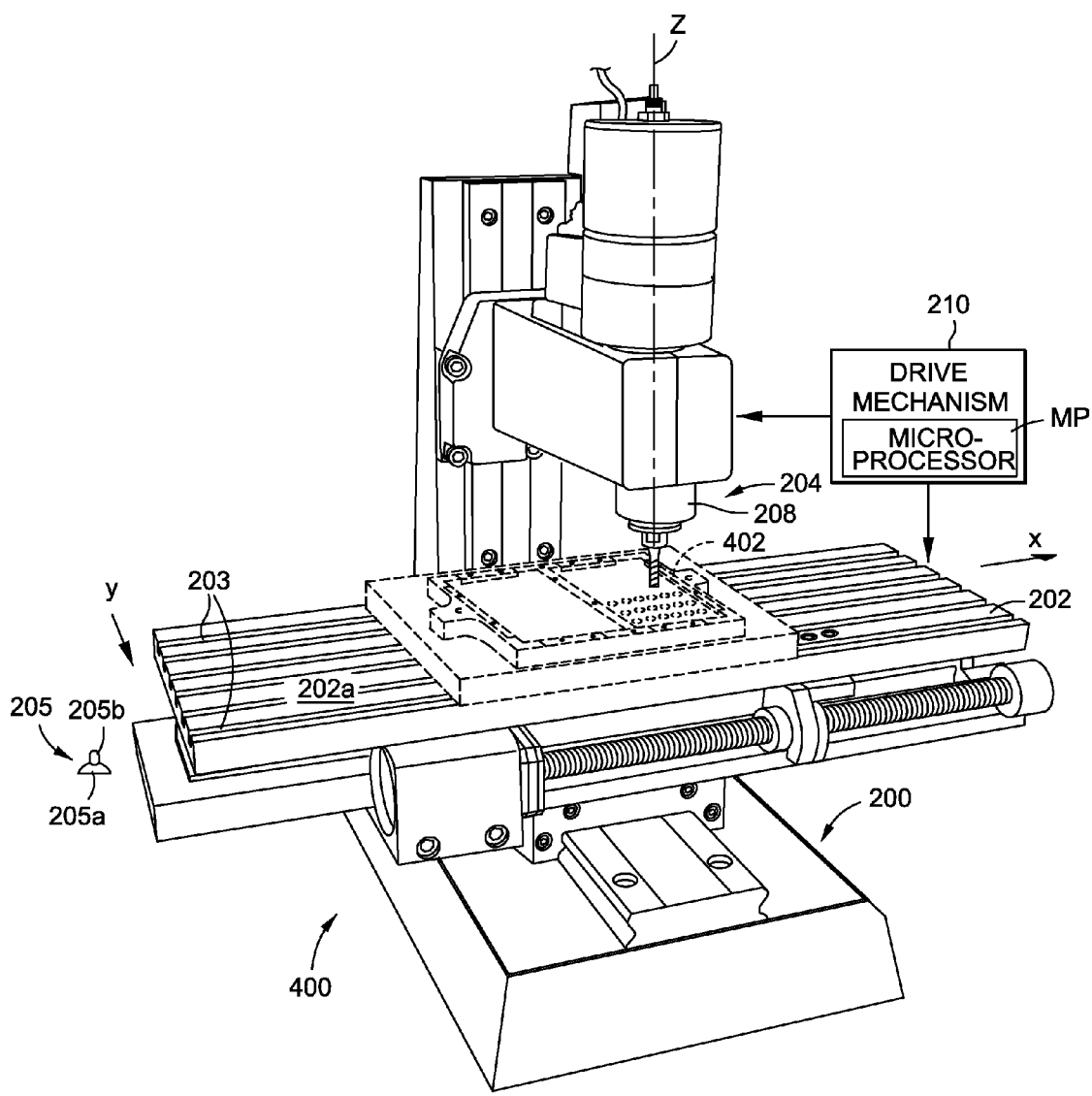
FIG. 10 is a perspective view of one embodiment of our apparatus comprising a conventional milling machine and our jig device (shown in dotted lines) attached to a platform mounted to the tabletop of the milling machine.

As shown in FIG. 10, the conventional milling machine 200 is modified by attaching to the tabletop 202 the platform 460, thus constructing our apparatus 400. Prior to conducting our method, the milling machine is calibrated (touching off) each time a drill bit 206 is coupled to the spindle 208 so the cutting tool 204 has at its start position an exact, predetermined spatial relationship with respect to the working reference plane WRP of the milling machine. Consequently, the machine 200 may be programmed to precisely cut from both sides of the work piece according to the milling pattern MP of the prosthesis being made. Using the appropriate reference milling plane as a guide, cutting tool 204 cuts into one side of a work piece to the optimum point of dissection OPD, the work piece is manually or automatically inverted, and then using the other reference milling plane as a guide, the cutting tool cuts into the other side of the work piece to the optimum point of dissection OPD.

Figure 3A:
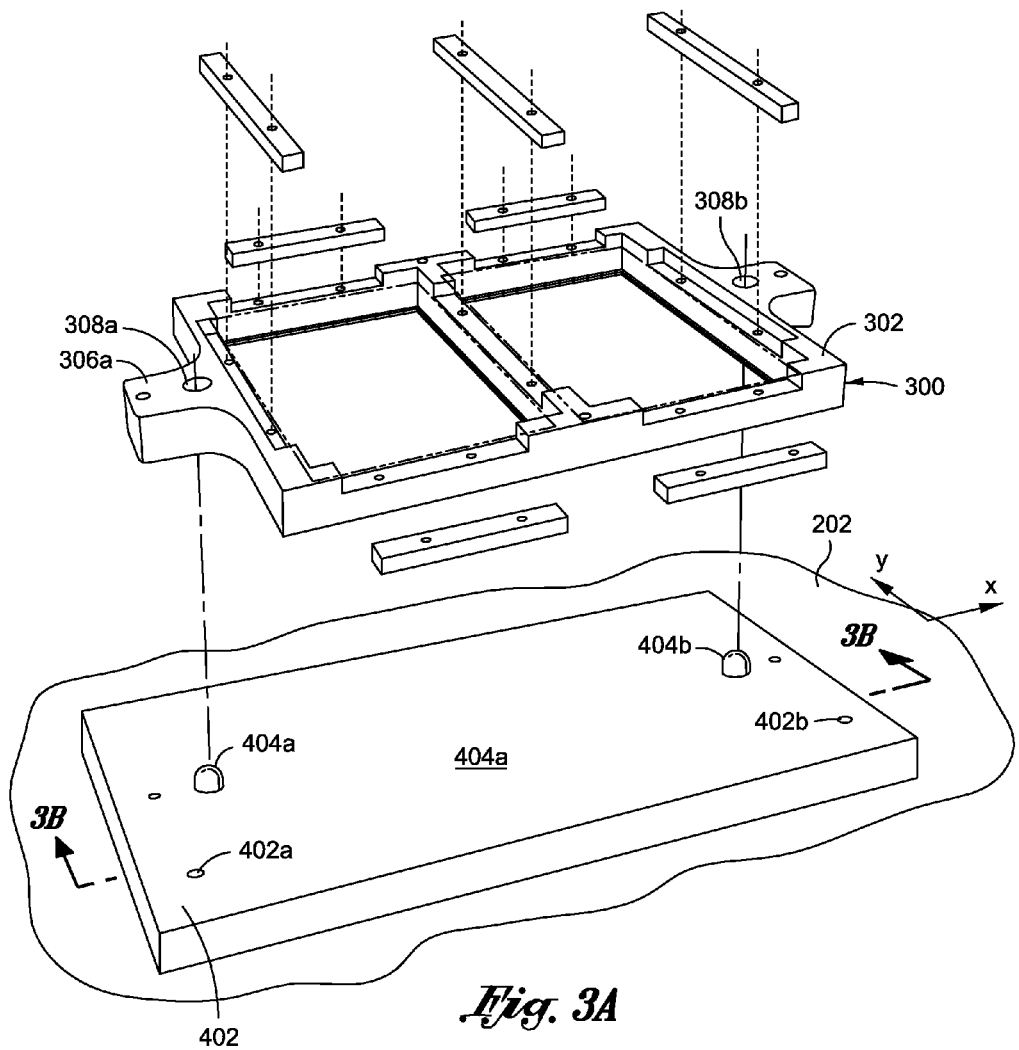
FIG. 3A is an exploded perspective view of portions of our apparatus with our jig device being attached to a tabletop of our apparatus.
Figure 3B:
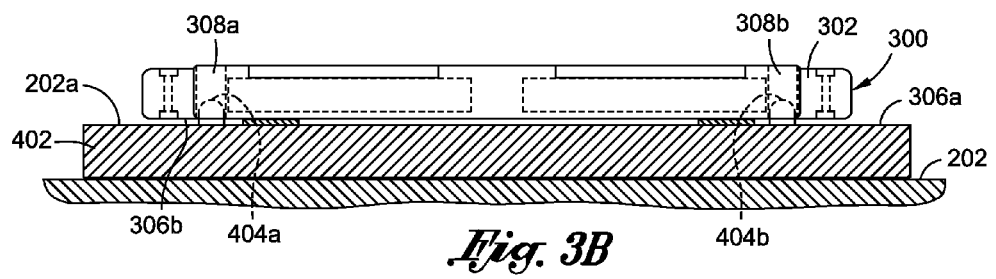
FIG. 3B is a cross-sectional view of portions of our apparatus showing our jig device attached to the tabletop of a milling machine.

As best illustrated in FIGS. 3A, 3B, and 10, our jig device 300 is held in a stationary position on the tabletop 202 so it moves laterally along with the movement of the tabletop. Although our jig device 300 may be fastened directly to the tabletop 202, in the one embodiment apparatus 400, it is mounted to the platform 402 that is bolted to the tabletop 202 in a precise fixed position on the tabletop. Aligned vertical post elements 404a and 404b project outward at a right angle from a flat horizontal surface 404a (FIG. 3A) of the platform 402. These post elements 404a and 404b interact with the alignment holes 308a and 308b in the frame member 302, so an individual post element slides into an individual hole, hole 308a or 308b, as the case may be, when our jig device 300 is mounted on the platform 402. In the embodiment depicted, the tabletop 202 has parallel T-slots 203 (FIG. 10) that provide a track for individual bolts 205, each bolt having a head 205a that slides along a selected T-slot. Threaded shafts 205b of these bolts 205 extend outward from the surface of the tabletop 202 through orifices 402a and 402b in the platform 402. When the platform 402 has been positioned on the tabletop 202 in a precise location for proper calibration, nuts (not shown) are screwed onto the threaded shafts extending through the orifices 402a and 402b to lock the platform in position. This alignment arrangement enables the jig device 300 to be precisely positioned on the tabletop 202, which is critical in milling the work piece so no surface defects are produced. As discussed above, the cutting tool 204 has at its start position an exact, predetermined spatial relationship with respect to the working reference plane WRP of the milling machine 200. Consequently, the machine 200 may be programmed to precisely cut from the work piece a prosthesis having a surface essentially free of defects by cutting from both sides of the work piece for each individual prosthesis being made.

With the cutting tool 204 in its start position and the jig device 300 properly located on the tabletop 202, the drive mechanism 210 for the milling machine 200 is initially operated. With the work piece in a first position presenting one side to the cutting tool, a substantial portion of material from this one side is drilled away while avoiding penetrating through the work piece with the tip 206a of the drill bit 206. This forms in the one side of the work piece a cavity, which as discussed above, is at least partially filled with a support material SM before or after removing the jig device 300 from its mounting to the platform 402. In this embodiment, our jig device 300 is manually removed and inverted and re-mounted to the platform to present the opposite side of the work piece to the cutting tool 204 for milling.

Because the drive mechanism 210 returns the cutting tool 204 and the tabletop 202 to their start positions after partially cutting through either side of the work piece, and because of the way in which the jig device 300 interacts with the post elements 404a and 404b, the initiation of the milling operation when cutting into either side of a work piece always occurs with the work piece in an exact predetermined position, except flipped over. Consequently, the milling machine may be programmed to precisely mill both sides of the work piece to make a prosthesis free of surface defects. As illustrated in FIG. 10, an electronic control system for the drive mechanism 210 of our apparatus has a programmable microprocessor MP.

FIGS. 11A Through 11D

In the embodiment shown in FIGS. 11A through 11D, a mounting mechanism 400 is employed to carry our jig device 300 and rotated it when required to invert the work pieces as discussed above. In this embodiment our jig device 300 is not removed from our apparatus.

The mounting mechanism 500 includes a pair of spaced apart vertical posts 502 and 504 each including a spindle 506 (only one shown) to which, respectively, the opposed ears 304a and 304b of the jig are attached. The drive mechanism 210 is operably connected to each of the spindles, for example, the spindle 506. Upon actuation of the drive mechanism 210, the spindle 506 rotates our jig through a 180° turn, inverting the jig.

SCOPE OF THE INVENTION

The above presents a description of the best mode we contemplate of carrying out our jig device and apparatus and method of making a prosthesis in such full, clear, concise, and exact terms as to enable a person skilled in the art to make and use. Our jig device and apparatus and method of making a prosthesis are, however, susceptible to modifications and alternate constructions from the illustrative embodiments discussed above which are fully equivalent. Consequently, it is not the intention to limit our jig device and apparatus and method of making a prosthesis to the particular embodiments disclosed. On the contrary, our intention is to cover all modifications and alternate constructions coming within the spirit and scope of our jig device and apparatus and method of making a prosthesis as generally expressed by the following claims, which particularly point out and distinctly claim the subject matter of our invention:

The invention claimed is:

1. A method wherein a milling machine cuts a prosthesis from a two-sided work piece held in a jig device, said method comprising, in sequence, the steps of inserting the jig device holding the work piece into the milling machine at a predetermined location so the jig device and milling machine are in an exact spatial relationship to enable the milling machine to precisely mill from the work piece a prosthesis having a surface essentially free of defects, partially milling through a first side of the work piece to form in the work piece a cavity having a surface part corresponding to at least a portion of the prosthesis being made removing the jig device from the milling machine and filling the cavity at least partially with a support material, presenting to the milling machine a second side of the work piece by inverting the jig device and reinserting the inverted jig device into the machine at said predetermined location, milling the work piece from said second side to form said prosthesis with a surface essentially free of defects, said prosthesis being supported within the work piece by the support material, and separating the prosthesis from the work piece, where the jig device and milling machine have interactive elements that enable the jig device to be repeatedly inserted, removed and inverted, and then reinserted into the milling machine at the same predetermined location with each insertion, or reinsertion after inverting, so the jig device and milling machine are always in the same exact spatial relationship to enable the cutting tool to precisely cut from the work piece a prosthesis having a surface essentially free of defects.

2. The method of claim 1 where the milling machine is programmed to cut into the work piece a maximum depth corresponding to substantially an optimum point of dissection of the prosthesis being made and no further.

3. The method of claim 2 where the jig device is substantially symmetrical about a central longitudinal line and substantially symmetrical about a central latitudinal line.

4. The method of claim 1 where the jig device includes a frame structure that holds the work piece.

5. The method of claim 4 where the frame structure has opposed planar parallel surfaces.

6. The method of claim 1 where the work piece is a substantially solid block having opposed, substantially parallel, planar sides.

7. The method of claim 6 where the work piece comprises a wax, metal, a ceramic, or a plastic.

8. The method of claim 1 where the jig device when inserted or reinserted into the milling machine is substantially oriented in a horizontal plane and the cutting tool is substantially oriented in a vertical plane.

9. The method of claim 1 where the jig device when inserted or reinserted into the milling machine is in a first plane and the cutting tool is at a right angle to said first plane.

10. The method of claim 1 where a floor of the cavity corresponds to the surface part corresponding to at least a portion of the prosthesis being made.

* * * * *